United States Patent [19]

Reller et al.

[11] 4,199,576

[45] Apr. 22, 1980

[54] ANALGESIC AND ANTI-INFLAMMATORY COMPOSITIONS FOR TOPICAL APPLICATION

[75] Inventors: Herbert H. Reller; Herbert C. Kretschmar, both of Cincinnati, Ohio

[73] Assignee: The Procter & Gamble Company, Cincinnati, Ohio

[21] Appl. No.: 2,477

[22] Filed: Jan. 10, 1979

Related U.S. Application Data

[63] Continuation-in-part of Ser. No. 750,935, Dec. 15, 1976, abandoned.

[51] Int. Cl.$^2$ .............................................. A61K 31/60
[52] U.S. Cl. .................................................... 424/230
[58] Field of Search ................................. 424/230, 234

[56] References Cited

U.S. PATENT DOCUMENTS

| 706,356 | 8/1902 | Summers | 424/230 |
|---|---|---|---|
| 749,980 | 1/1904 | Balthazard | 424/230 |
| 1,436,304 | 11/1922 | Burdick et al. | 424/230 |
| 2,474,005 | 6/1949 | Martin et al. | 260/474 |
| 2,975,097 | 3/1961 | Modderno | 424/234 |
| 3,119,739 | 1/1964 | Campbell | 424/234 |
| 3,518,297 | 6/1970 | Busacca | 260/480 |

FOREIGN PATENT DOCUMENTS 1220447  1/1971  United Kingdom .
1379009  1/1975  United Kingdom .

*Primary Examiner*—Stanley J. Friedman
*Attorney, Agent, or Firm*—Jerry J. Yetter; Jack D. Schaeffer; Richard C. Witte

[57] ABSTRACT

Compositions containing salicylic acid derivatives are useful for topical application to the skin. The compositions are especially effective for providing an anti-inflammatory effect.

30 Claims, No Drawings

ANALGESIC AND ANTI-INFLAMMATORY COMPOSITIONS FOR TOPICAL APPLICATION

CROSS REFERENCE TO RELATED APPLICATION

This application is a continuation-in-part of U.S. application Ser. No. 750,935, filed Dec. 15, 1976, now abandoned.

BACKGROUND OF THE INVENTION

This invention relates to the use of salicylic acid derivatives. More particularly, it relates to compositions containing salicylic acid derivatives, and the topical use thereof on animals, including man, for providing an anti-inflammatory effect.

Tissue inflammation is the result of interconnected physiological events. Inflammation of the skin which is associated with tissue damage can result from various skin disorders such as eczema, psoriasis, seborrheic dermatitis, contact dermatitis, allergic dermatitis, etc. Inflammation is also associated with tissue damage resulting from ultraviolet or thermal burns, attack by certain micro-organisms, insect bites, stings, etc. Inflammation of deeper structures, the muscles, tendons, bursa, and joints, which is associated with tissue damage, can result from physical trauma, e.g. sprains, strains, contusions, strenuous exercise, etc. Such inflammation may result in bursitis, tendinitis, and muscle soreness. Inflammation is also associated with tissue damage resulting from metabolic disorders, such as gout, or from immunologic disorders, such as rheumatoid arthritis, or from changes associated with aging, such as osteoarthritis.

Symptoms of inflammation are erythema (redness), edema (swelling), heat, pain, and loss of function. The immediate consequence of tissue damage is the release of certain chemical agents which are mediators of inflammation, i.e. these materials evoke and intensify the events which result in the redness, swelling, pain and heat. Examples of these chemical agents are histamine, seratonin and the kinins.

One of the important mediators of inflammation are certain prostaglandins. In contrast to histamine, seratonin and the kinins, the prostaglandins are continuously biosynthesized and released from cells at the inflammatory site. Thus, the prostaglandins have a longer lasting effect. Various anti-inflammatory compounds are known inhibitors of prostaglandin synthesis. One commonly used anti-inflammatory drug is aspirin. Aspirin, of course, is a well known oral drug; however, recent studies have also indicated aspirin can delay and decrease inflammation in animals and in humans when applied topically. However, it has been found that a relatively high concentration of aspirin must be topically applied before it is effective for its intended function. Unfortunately, the repeated use of a high level of aspirin causes primary irritation and peeling of the superficial layers (the stratum corneum) of the skin. Accordingly, there is a need for a compound to be used topically which will alleviate inflammation without adverse secondary effects.

Various esters of acetylsalicylic acid have been suggested for oral or parenteral use to provide an anti-inflammatory effect. (For example, see U.S. Pat. Nos. 749,980; 1,436,304; 2,474,005; 3,518,297 and British Pat. No. 1,379,009.) However, it has been found that oral or parenteral administration of the esters of acetylsalicylic acid does not provide satisfactory anti-inflammatory effects. It is believed the esters decompose prior to arriving at the site of inflammation or are poorly absorbed into the blood.

Accordingly, it is an object of this invention to provide compositions which are useful as anti-inflammatory agents.

It is another object of this invention to provide compositions which can be topically applied to skin to alleviate inflammation.

It is still another object of this invention to provide a composition containing a salicylic acid derivative which can be efficiently and effectively used for topical application.

A still further object of this invention is to provide a method of topically administering to skin a composition capable of alleviating inflammation in various skin disorders associated with disease and trauma and also various disorders of the deeper structures, muscles, tendons, bursa and joints associated with the disease and trauma.

These and other objects will become apparent from the description to follow.

As used herein all percents and ratios are by weight unless otherwise indicated.

SUMMARY OF THE INVENTION

A composition for topical application to skin to alleviate inflammation consisting essentially of:

(a) an effective amount of a salicylic acid derivative of the formula

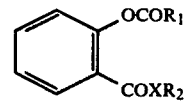

where $R_1$ is an alkyl group having from 1 to 4 carbon atoms, X is O, NH or $NR_2$ and $R_2$ is a saturated or unsaturated aliphatic group having from 4 to 10 carbon atoms, benzyl or phenyl; and (b) the balance a pharmaceutically acceptable carrier having dissolved or dispersed therein the salicylic acid derivative, said carrier being capable of delivering the salicylic acid derivative to the skin and capable of resisting removal by water for a length of time sufficient for the salicylic acid derivative to penetrate into the skin.

A method is also provided for reducing inflammation by topically applying an effective amount of the salicylic acid derivative to the epidermal area so affected.

DETAILED DISCUSSION

The compositions herein consist essentially of a salicylic acid derivative and a pharmaceutically acceptable carrier. Each of the components and the method of using the composition are described hereinafter.

Salicylic acid derivatives useful herein for topical application to skin have the following formula

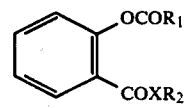

wherein $R_1$ is an alkyl group having from 1 to 4 carbon atoms, X is O, NH or $NR_2$ and $R_2$ is a saturated or unsaturated aliphatic group having from 4 to 10 carbon atoms, benzyl or phenyl. The saturated or unsaturated aliphatic group includes alkyl, alkenyl, alkadienyl, alkatrienyl, alkynyl and alkadiynyl groups.

As used herein the groups represented by $R_2$ can be substituted with acetoxy; alkyloxy, e.g. methoxy, ethoxy and butoxy; alkylamido; halogen, e.g. chloro, bromo and fluoro; amino; nitro; alkyl, e.g. methyl, ethyl and butyl; amido; and hydroxy moieties without adversely affecting the efficacy of the salicylic acid derivative. Such moieties can be in the ortho, meta or para positions when $R_2$ is benzyl or phenyl.

In general, the compounds herein are prepared from salicylic acid. The salicylic acid is initially acylated with an appropriate anhydride of the formula $(RCO)_2O$ wherein R has from 1 to 4 carbon atoms. Examples of the anhydride are acetic anhydride, propionic anhydride, butyric anhydride, valeric anhydride and pivalyl anhydride. The reaction proceeds in the presence of sulfuric acid at a temperature from 40° C. to 80° C. The resultant acyloxy benzoic acid is next reacted to form an ester or an amide thereof. The ester is formed by reacting the acyloxy benzoic acid with oxalyl chloride or sulfonyl chloride to provide acyloxy benzoyl chloride. This compound is then reacted with a suitable alcohol in the presence of pyridine to provide the desired ester. Suitable alcohols include primary, secondary and tertiary -butanol, -pentanol, -hexanol, -heptanol and -octanol; unsaturated alcohols, e.g. 2-butenol, 2-hexenol, 4-hexenol, 2-octenol and 3-octenol; benzyl alcohol; and phenol.

The amide compounds of the present invention, i.e. when Y is NH or $NR_2$ are provided by reacting the acyloxy benzoyl chloride with a suitable amine. This reaction occurs at a temperature of 0° C. to 30° C.

Preferred salicylic acid derivatives are those wherein X is O. More preferred salicylic acid derivatives are those wherein X is O, $R_1$ is methyl or tertiary butyl, and $R_2$ is an alkyl group or benzyl. Highly preferred compounds are benzyl 2-acetoxybenzoate and hexyl 2-acetoxybenzoate.

The following compounds are exemplary salicylic acid derivatives.
Butyl 2-acetoxybenzoate
Hexyl 2-acetoxybenzoate
2'-ethylhexyl 2-acetoxybenzoate
Octyl 2-acetoxybenzoate
Pentyl 2-propionoxybenzoate
Octyl 2-propionoxybenzoate
Hexyl 2-pivaloxybenzoate
Hexyl 2-butyroxybenzoate
2',5'-Hexadienyl 2-acetoxybenzoate
2'-Hexenyl 2-acetoxybenzoate
Benzyl 2-butyroxybenzoate
Benzyl 2-acetoxybenzoate
Benzyl 2-pivaloxybenzoate
Phenyl 2-acetoxybenzoate
2-Acetoxy-N-hexylbenzamide
2-Propionoxy-N-octylbenzamide
2-Acetoxy-N,N-dibutylbenzamide
p-Acetamidophenyl 2-acetoxybenzoate
5'-Hydroxyhexyl 2-acetoxybenzoate
6'-Acetoxyhexyl 2-acetoxybenzoate
6'-Fluorohexyl 2-acetoxybenzoate
6'-Nitrohexyl 2-acetoxybenzoate
6'-Methylamidohexyl 2-acetoxybenzoate
2'-Ethyl-2',5'-hexadienyl 2-acetoxybenzoate
2'-Acetoxybenzyl 2-propionoxybenzoate
2'-Fluorobenzyl 2-acetoxybenzoate
2'-Hydroxybenzyl 2-acetoxybenzoate
2'-Methoxybenzyl 2-acetoxybenzoate
2',4'-Diacetoxybenzyl 2-acetoxybenzoate
2'-Acetamidobenzyl 2-acetoxybenzoate The compositions contain an effective amount, preferably from 0.001% to 10% of the salicylic acid derivative. The balance of a composition consists essentially of a pharmaceutically acceptable carrier. Suitable carriers for the salicylic acid derivatives remain in place on the skin as a continuous film and resist being washed off easily by perspiration or by immersion in water. Generally, the carrier is organic in nature and capable of having dispersed or dissolved therein the salicylic acid derivative. Lotions, creams, solutions, gels and solids are common physical forms of the compositions herein. More detailed description of such forms follows.

LOTIONS

Lotions consist essentially of from 0.001% to 10%, preferably 0.01% to 5% of the salicylic acid derivative, from 1% to 25%, preferably 3% to 15% of an emollient, and the balance water. Several emollients are known. Examples of classes of emollients and examples thereof follow.

1. Hydrocarbon oils and waxes. Examples thereof are mineral oil, petrolatum, parrafin, ceresin, ozokerite, microcrystalline wax, polyethylene, and perhydrosqualene.

2. Silicone oils, such as dimethyl polysiloxanes, methylphenyl polysiloxanes, water-soluble and alcohol-soluble silicone glycol copolymers.

3. Triglyceride esters, for example vegetable and animal fats and oils. Examples include castor oil, safflower oil, cottonseed oil, corn oil, olive oil, cod liver oil, almond oil, avocado oil, palm oil, sesame oil, and soybean oil.

4. Acetoglyceride esters, such as acetylated monoglycerides.

5. Ethoxylated glycerides, such as ethoxylated glyceryl monostearate.

6. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

7. Alkenyl esters of fatty acids having 10 to 20 carbon atoms. Examples thereof include oleyl myristate, oleyl stearate, and oleyl oleate.

8. Fatty acids having 10 to 20 carbon atoms. Suitable examples include pelargonic, lauric, myristic, palmitic, stearic, isostearic, hydroxystearic, oleic, linoleic, ricinoleic, arachidic, behenic, and erucic acids.

9. Fatty alcohols having 10 to 20 carbon atoms. Lauryl, myristyl, cetyl, hexadecyl, stearyl, isostearyl, hydroxystearyl, oleyl, ricinoleyl, behenyl, erucyl, and 2-octyl dodecanol alcohols are examples of satisfactory fatty alcohols.

10. Fatty alcohol ethers. Ethoxylated fatty alcohols of 10 to 20 carbon atoms include the lauryl, cetyl, stearyl, isostearyl, oleyl, and cholesterol alcohols having attached thereto from 1 to 50 ethylene oxide groups or 1 to 50 propylene oxide groups.

11. Ether-esters such as fatty acid esters of ethoxylated fatty alcohols.

12. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

13. Polyhydric alcohols and polyether derivatives. Propylene glycol, dipropylene glycol, polypropylene glycol 2000, 4000, polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol 200–6000, methoxy polyethylene glycols 350, 550, 750, 2000, 5000, poly[ethylene oxide] homopolymers (100,000–5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), $C_{15}$–$C_{18}$ vicinal glycol, and polyoxypropylene derivatives of trimethylolpropane are examples thereof.

14. Polyhydric alcohol esters. Ethylene glycol mono- and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

15. Wax esters such as beeswax, spermaceti, myristyl myristate, stearyl stearate.

16. Beeswax derivatives, e.g. polyoxyethylene sorbitol beeswax. These are reaction products of beeswax with ethoxylated sorbitol of varying ethylene oxide content, forming a mixture of ether-esters.

17. Vegetable waxes including carnauba and candelilla waxes.

18. Phospholipids such as lecithin and derivatives.

19. Sterols. Cholesterol, cholesterol fatty acid esters are examples thereof.

20. Amides such as fatty acid amides, ethoxylated fatty acid amides, solid fatty acid alkanolamides.

The lotions of this invention can also further consist essentially of from 1% to 10%, preferably 2% to 5% of an emulsifier. Emulsifiers are of a nonionic, anionic or cationic class. Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene glycol wherein the fatty acid moiety contains from 10 to 20 carbon atoms, fatty acid monoglyceride wherein the fatty acid moiety contains from 10 to 20 carbon atoms, diethylene glycol, polyethylene glycols of molecular weight 200 to 6000, propylene glycol of molecular weight 200 to 3000, glycerol, sorbitol, sorbitan, polyoxyethylene sorbitol, polyoxyethylene sorbitan, and hydrophilic wax esters. Suitable anionic emulsifiers include the fatty acid soaps, e.g. sodium, potassium and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Satisfactory cationic emulsifiers are the quaternary ammonium, morpholinium and pyridinium compounds. Certain of the emollients described in preceeding paragraphs also have emulsifying properties. When a lotion is formulated containing such an emollient, an additional emulsifier is not needed, though it can be included in the composition.

The balance of the composition is water. The lotions can be formulated by simply admixing all of the components together. Preferably the salicylic acid derivative is dissolved in the emollient and the mixture is added to the water. Optional components such as the emulsifier or common additives can be included. One common additive is a thickening agent at a level from 1% to 10% of the composition. Examples of suitable thickening agents include: cross-linked carboxy polymethylene polymers, methyl cellulose, polyethylene glycols, gum tragacanth, gum kharaya, xanthan gums and bentonite.

CREAMS

Compositions of this invention also are formulated in a cream form. The creams consist essentially of from 0.001% to 10%, preferably 0.01% to 5% of the salicylic acid derivative, from 5% to 50%, preferably 10% to 25% of an emollient, and the balance water. The emollients above described are also used in the cream form of the composition. Optionally the cream form contains a suitable emulsifier. Emulsifiers described above are useful herein. When an emulsifier is included, it is in the composition at a level from 3% to 50%, preferably 5% to 20%.

SOLUTIONS

The compositions of this invention are also formulated in a solution form. The solution form of the composition consists essentially of from 0.001% to 10%, preferably 0.01% to 5% of the salicylic acid derivative and the balance a suitable organic solvent. Suitable organic materials useful as the solvent or a part of a solvent system are as follows: propylene glycol, polyethylene glycol (200–600) polypropylene glycol (425–2025), glycerine, sorbitol esters, 1,2,6-hexanetriol, ethanol, isopropanol, diethyl tartrate, butanediol, and mixtures thereof. Such solvent systems can also contain water.

These compositions are applied to the skin in the solution form, or the solutions are formulated in an aerosol form and applied to the skin as a spray-on. The compositions in the aerosol form additionally consist essentially of from 25% to 80%, preferably 30% to 50% of a suitable propellant. Examples of such propellants are: the chlorinated, fluorinated and chlorofluorinated lower molecular weight hydrocarbons. Nitrous oxide and carbon dioxide are also used as propellant gases. They are used at a level sufficient to expel the contents of the container.

GELS

Compositions herein are formulated into a gel form by simply admixing a suitable thickening agent to the above-described solution compositions. Examples of suitable thickening agents are described above with respect to the lotions.

The gelled compositions consist essentially of from 0.001% to 10%, preferably 0.01% to 5% of the salicylic acid derivative; from 5% to 75%, preferably 10% to 50% of an organic solvent as above described; from 0.5% to 20%, preferably 1% to 10% of the thickening agent; and the balance water.

SOLIDS

The compositions of this invention are also formuated into a solid form. Such forms have use as a stick-type composition intended for application to the lips or other parts of the body. Such compositions consist essentially of from 0.001% to 10%, preferably 0.01% to 5% of the salicylic acid derivative and from 50% to 98%, preferably 60% to 90% of the above described emollient. This composition can further consist essentially of from 1% to 20%, preferably 5% to 15% of a suitable thickening agent, and optionally emulsifiers and water. Thickening agents as described above with respect to the gelled compositions are suitable herein.

Additives commonly found in topical compositions such as preservatives, e.g. methyl and ethyl-paraben, dyes and perfume can be included in any of the aforedescribed compositions.

METHOD OF APPLICATION

The effective amount of the salicylic acid derivative used topically will vary with the particular circumstances of application, the duration of the anticipated exposure, and like considerations. Generally, from 0.01 $\mu$g to 500 $\mu$g salicylic acid derivative per square centimeter of epidermal area is applied. Single applications for treatment of inflammation of the skin preferably range from 0.01 $\mu$g to 50 $\mu$g of the salicylic acid derivative per square centimeter of epidermal area. Greater amounts are uneconomical and provide no noticeable increased activity while lesser amounts do not provide a noticeable beneficial effect. Single applications for treatment of inflammation of deeper structures preferably range from 0.1 $\mu$g to 500 $\mu$g salicylic acid derivative per square centimeter of epidermal area. It is to be understood the amount of topical composition (salicylic acid derivative plus carrier) applied to the affected epidermal areas can be easily determined based on the amount of salicylic acid derivative contained therein.

Topical application of the salicylic acid derivatives described herein are effective for treating inflammation, yet the side effects encountered with the oral delivery of known anti-inflammatory agents are avoided. This is particularly true with the treatment of some forms of inflammation such as that associated with arthritis wherein higher doses are needed. Unwanted side effects encountered with oral agents include nausea, stomach lesions, ulceration, blood loss, etc. Topical application of the salicylic acid derivatives described herein is believed to be much more effective than oral delivery because the derivatives are less likely to decompose prior to arriving at the site of inflammation and/or are more fully absorbed into the bloodstream.

The following examples are illustrative of the compositions herein and their manner of use.

EXAMPLE I

The compositions of this invention are evaluated for their anti-inflammation properties using a guinea pig ultraviolet light induced erythema test.

Hartley strain albino guinea pigs weighing between 400 and 500 grams are clipped on the dorsal area and then depilated using a cream hair remover. 15 minutes after the application of the hair remover, the area is thoroughly washed using warm tap water and then dried with a towel. After a period of about 18 hours, the guinea pigs are irradiated in a wire cage for 30 minutes using a bank of four FS 40 Westinghouse lights at a distance of 31 cm. Ten minutes irradiation constitutes a minimal erythema dose. An adhesive tape strip is attached to the center of the guinea pig's back to retain an unirradiated portion of skin. About 1 hour after irradiation time, 3 preparations are applied on each side using a micropipette. The treated areas are about 1$\times$4 cm in size and are aligned vertically from near the center back down the side. The degree of blanching is determined at hourly intervals. Blanching is graded on a 0–4 scale with 0 being no blanching and 4 being total blanching.

Evaluations of the anti-inflammatory activities of the salicylic acid derivatives are made by comparing the cumulative blanching grades over a 1–4 hour period after application of varying concentrations of the salicylic acid derivatives in different carriers. The figures in the column labeled "A" are obtained from compositions containing 1.0% of the compound being tested in a 1:1 mixture of propylene glycol and ethanol, and in the column labeled "B" are obtained from compositions containing 1.0% of the compound being tested in ethanol. The higher the blanching grade, the greater is the compound's activity. The table that follows shows the cumulative blanching grades of different salicylic acid derivatives and hydrocortisone. The maximum 1–4 hour blanching grade is 16 while no blanching is 0.

| Compound | 1-4 Hour Cumulative Blanching Grades | |
| --- | --- | --- |
| | A | B |
| Methyl 2-acetoxybenzoate | 0 | |
| Hexyl 2-acetoxybenzoate | 10.3 | |
| Octyl 2-acetoxybenzoate | 6.0 | |
| Decyl 2-acetoxybenzoate | 7.5 | |
| Dodecyl 2-acetoxybenzoate | 1.8 | |
| Oleyl 2-acetoxybenzoate | 0 | |
| Benzyl 2-acetoxybenzoate | 11.1 | |
| Benzyl 2-propionoxybenzoate | | 9.9 |
| Benzyl 2-pivaloxybenzoate | | 6.7 |
| Aspirin | 4.0 | |
| Hydrocortisone | 4.0 | |

The above results show compounds within the scope of the invention, i.e. the hexyl-, octyl-, decyl- and benzyl-2-acetoxybenzoate, benzyl 2-propionoxybenzoate and benzyl 2-pivaloxybenzoate have greater activity than aspirin, hydro-cortisone and salicylic acid esters not falling within the scope of this invention.

Additionally, the anti-inflammation activity of the salicylic acid derivatives is determined by calculating their $IC_{50}$ values. That is, compounds commonly show a dose-response relationship such that higher concentrations produce a greater response and lower concentrations a lower response. However, different compounds have steeper or flatter slopes of their dose-response curves so that comparison of activity at one or a few concentrations does not give a realistic understanding of their relative activities. In order to better relate the activity of several compounds by a single number, the concentration of compound which inhibits a function by 50% is calculated from the dose-response curve. This term is called the $IC_{50}$, (the concentration which inhibits the function by 50%). In the following table the $IC_{50}$ refers to concentrations (expressed in millimoles) of the salicylic acid derivative which inhibits UV-induced erythema by 50%. These $IC_{50}$ data are based on cumulative blanching grades over a 1-4 hour period after application of the salicylic acid derivative. The lower the $IC_{50}$ value, the greater is the compound's activity. The salicylic acid derivative is applied from a 1:1 mixture of propylene glycol and ethanol.

|  | $IC_{50}$ |
|---|---|
| Benzyl 2-acetoxybenzoate | 1.0 |
| Hexyl 2-acetoxybenzoate | 2.0 |
| Hydrocortisone | 28.0 |
| Aspirin | 140.0 |

The compositions in the following examples are exemplary of various composition forms.

EXAMPLE II

| Lotion | |
|---|---|
| Isopropyl myristate | 8% |
| Corn oil | 5% |
| Propylene glycol | 5% |
| Triethanolamine oleate | 5% |
| Benzyl 2-acetoxybenzoate | 0.25% |
| Xanthan gum | 0.5% |
| Water | Balance |

| Cream | |
|---|---|
| Isopropyl myristate | 3% |
| Sorbitol | 5% |
| Propylene glycol | 10% |
| Triethanolamine stearate | 17% |
| Hexyl 2-acetoxybenzoate | 1% |
| Water | Balance |

| Gel | |
|---|---|
| Oleyl alcohol | 1% |
| Propylene glycol | 19% |
| Butyl 2-propionoxybenzoate | 2% |
| Triethanolamine | 0.5% |
| Ethanol | 57% |
| Carbopol 940* | 0.5% |
| Water | Balance |

*Carbopol 940 is a carboxy vinyl polymer available from the B.F. Goodrich Chemical Co.

| Solution | |
|---|---|
| Propylene glycol | 10% |
| Polyethylene glycol 400 | 2% |
| Benzyl 2-acetoxybenzoate | 0.5% |
| Ethanol | 48% |
| Water | Balance |

| Ointment | |
|---|---|
| Oleyl alcohol | 30% |
| Cetyl alcohol | 40% |
| Propylene glycol | 26% |
| Phenyl 2-acetoxybenzoate | 4% |

What is claimed is:

1. A composition for topical application to skin to alleviate inflammation, consisting essentially of:
   (a) an effective amount of a salicylic acid derivative of the formula

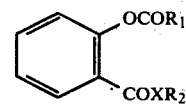

where $R_1$ is an alkyl group having from 1 to 4 carbon atoms, X is O, NH or $NR_2$ and $R_2$ is a saturated or unsaturated aliphatic group having from 4 to 10 carbon atoms, benzyl or phenyl; and
   (b) the balance a pharmaceutically acceptable carrier having dissolved or dispersed therein the salicylic acid derivative, said carrier being capable of delivering the salicylic acid derivative to the skin and capable of resisting removal by water for a length of time sufficient for the salicylic acid derivative to penetrate into the skin.

2. The composition of claim 1 wherein the composition consists essentially of from 0.001% to 10% of the salicylic acid derivative.

3. The composition of claim 2 wherein X is O.

4. The composition of claim 3 wherein $R_2$ is an alkyl group.

5. The composition of claim 3 wherein $R_2$ is an alkenyl group.

6. The composition of claim 3 wherein $R_2$ is benzyl.

7. The composition of claim 3 wherein $R_2$ is phenyl.

8. The composition of claim 2 wherein X is NH or $NR_2$.

9. The composition of claim 4 wherein the salicylic acid derivative is hexyl 2-acetoxybenzoate.

10. The composition of claim 6 wherein the salicylic acid derivative is benzyl 2-acetoxybenzoate.

11. The composition of claim 2 wherein the composition is in the form of a lotion consisting essentially of:
   (a) the salicylic acid derivative;
   (b) from 1% to 25% of an emollient; and
   (c) the balance water.

12. The composition of claim 11 further consisting essentially of from 1% to 10% of an emulsifier.

13. The composition of claim 2 wherein the composition is in the form of a cream consisting essentially of:
   (a) the salicylic acid derivative;
   (b) from 5% to 50% of an emollient; and
   (c) the balance water.

14. The composition of claim 13 further consisting essentially of from 3% to 50% of an emulsifier.

15. The composition of claim 2 wherein the composition in the form of a solution consisting essentially of:
   (a) the salicylic acid derivative; and
   (b) the balance an organic solvent.

16. The composition of claim 2 wherein the composition is in the form of a gel consisting essentially of:
   (a) the salicylic acid derivative;

(b) from 5% to 75% of an organic solvent;
(c) from 0.5% to 20% of a thickening agent; and
(d) the balance water.

17. The composition of claim 2 wherein the composition is in the form of a solid consisting essentially of:
(a) the salicylic acid derivative; and
(b) from 50% to 98% of an emollient.

18. A method of topically alleviating inflammation, comprising applying to the epidermal area so affected an effective amount of a salicylic acid derivative of formula

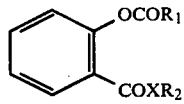

where $R_1$ is an alkyl group having from 1 to 4 carbon atoms, X is O, NH or $NR_2$ and $R_2$ is a saturated or unsaturated aliphatic group having from 4 to 10 carbon atoms, benzyl or phenyl.

19. The method of claim 18 wherein a composition consisting essentially of from 0.001% to 10% of the salicylic acid derivative and the balance a pharmaceutically acceptable carrier having dissolved or dispersed therein the salicylic acid derivative is applied to the epidermal area.

20. The method of claim 19 wherein from 0.01 μg to 500 μg of the salicylic acid derivative is applied per square centimeter of epidermal area.

21. The method of claim 20 wherein X is O.

22. The method of claim 21 wherein $R_2$ is an alkyl group.

23. The method of claim 21 wherein $R_2$ is an alkenyl group.

24. The method of claim 21 wherein $R_2$ is benzyl.

25. The method of claim 21 wherein $R_2$ is phenyl.

26. The method of claim 20 where X is NH or $NR_2$.

27. The method of claim 22 wherein the salicylic acid derivative is hexyl 2-acetoxybenzoate.

28. The method of claim 24 wherein the salicylic acid derivative is benzyl 2-acetoxybenzoate.

29. The method of claim 20 wherein inflammation of skin is treated with from 0.01 μg to 50 μg of the salicylic acid derivative per square centimeter of epidermal area.

30. The method of claim 20 wherein inflammation of muscles, tendons, bursa or joints is treated with from 0.1 μg to 500 μg of the salicylic acid derivative per square centimeter of epidermal area.

* * * * *